US00PP17705P2

(12) United States Plant Patent
Olesen et al.

(10) Patent No.: US PP17,705 P2
(45) Date of Patent: May 8, 2007

(54) ***CLEMATIS* PLANT NAMED 'EVIPO001'**

(50) Latin Name: *Clematis viticella*
Varietal Denomination: EVIpo001

(75) Inventors: Mogens N. Olesen, Fredensborg (DK); Raymond J. Evison, Guernsey (GB)

(73) Assignee: Poulsen Roser A/S, Fredensborg (DK)

( * ) Notice: Subject to any disclaimer, the term of this patent is extended or adjusted under 35 U.S.C. 154(b) by 512 days.

(21) Appl. No.: 10/719,750

(22) Filed: Nov. 21, 2003

(51) Int. Cl.
*A01H 5/00* (2006.01)

(52) U.S. Cl. ..... Plt./228

(58) Field of Classification Search ..... Plt./228, Plt./328

See application file for complete search history.

*Primary Examiner*—Kent Bell

(57) ABSTRACT

A new *Clematis* cultivar which is well suited to propagation in glasshouses. With a tall growth habit, profuse, violet blue flowers, and continuous summer flowering. The variety successfully propagates from softwood cuttings and is suitable for cultivation in commercial glasshouses. This new and distinct variety has shown to be uniform and stable in the resulting generations from asexual propagation.

2 Drawing Sheets

SUMMARY OF THE INVENTION

Botanical classification: *Clematis l.* Genus—*Clematis.* Species—*viticella.*

Variety denomination: 'EVIpo001'.

Commercial classification: Summer Flowering Cultivar.

The present invention constitutes a new and distinct variety of *Clematis* which originated from a chance pollination between the female seed parent an unnamed, non-patented plant and an unknown male pollen parent plant.

The new *clematis* may be distinguished from its female seed parent by the following combination of characteristics:

1. The seed parent has purple flowers. 'EVIpo001' has violet blue flowers.
2. The seed parent has a white flower center. 'EVIpo001' has a yellow center.

The seed resulting from the chance pollination was planted in a controlled environment. The new variety is named 'EVIpo001'.

The objective of the selection of this *Clematis* variety for commercial glasshouse and nursery culture was to create a new and distinct variety with:

1. Profusion of light violet flowers;
2. Summer flowering;
3. Yellow flower center;
4. Vigorous growth habit.

These qualities required improvement in *Clematis* varieties that were in commercial cultivation and the objectives have been substantially achieved in the new variety, as evidenced by the unique combination of characteristics that are present in 'EVIpo001' which distinguish it from all other varieties of which we are aware.

The seeds from the aforementioned chance pollination were germinated and evaluations of the resulting seedling plants were conducted in a controlled environment. As a result, 'EVIpo001' was selected by Raymond J. Evison and Mogens N. Olesen in their *Clematis* development program in Domarie Vineries Les Sauvagees, St. Sampsons, Guernsey, Channel Islands, United Kingdom in April of 1997.

Asexual reproduction of 'EVIpo001' by cuttings was first done by Raymond J. Evison and Mogens N. Olesen in Domarie Vineries Les Sauvagees, St. Sampsons, Guernsey, Channel Islands, United Kingdom in June of 1997. This initial and subsequent propagations have demonstrated that the characteristics of 'EVIpo001' are true to type and are transmitted from one generation to the next.

BRIEF DESCRIPTION OF THE DRAWING

The accompanying color illustration show as true as it is reasonably possible to obtain in color photographs of this type. Specifically illustrated in SHEET 1.

Specifically illustrated in SHEET 2.

Figures 1, 2, 3, 4, 5:
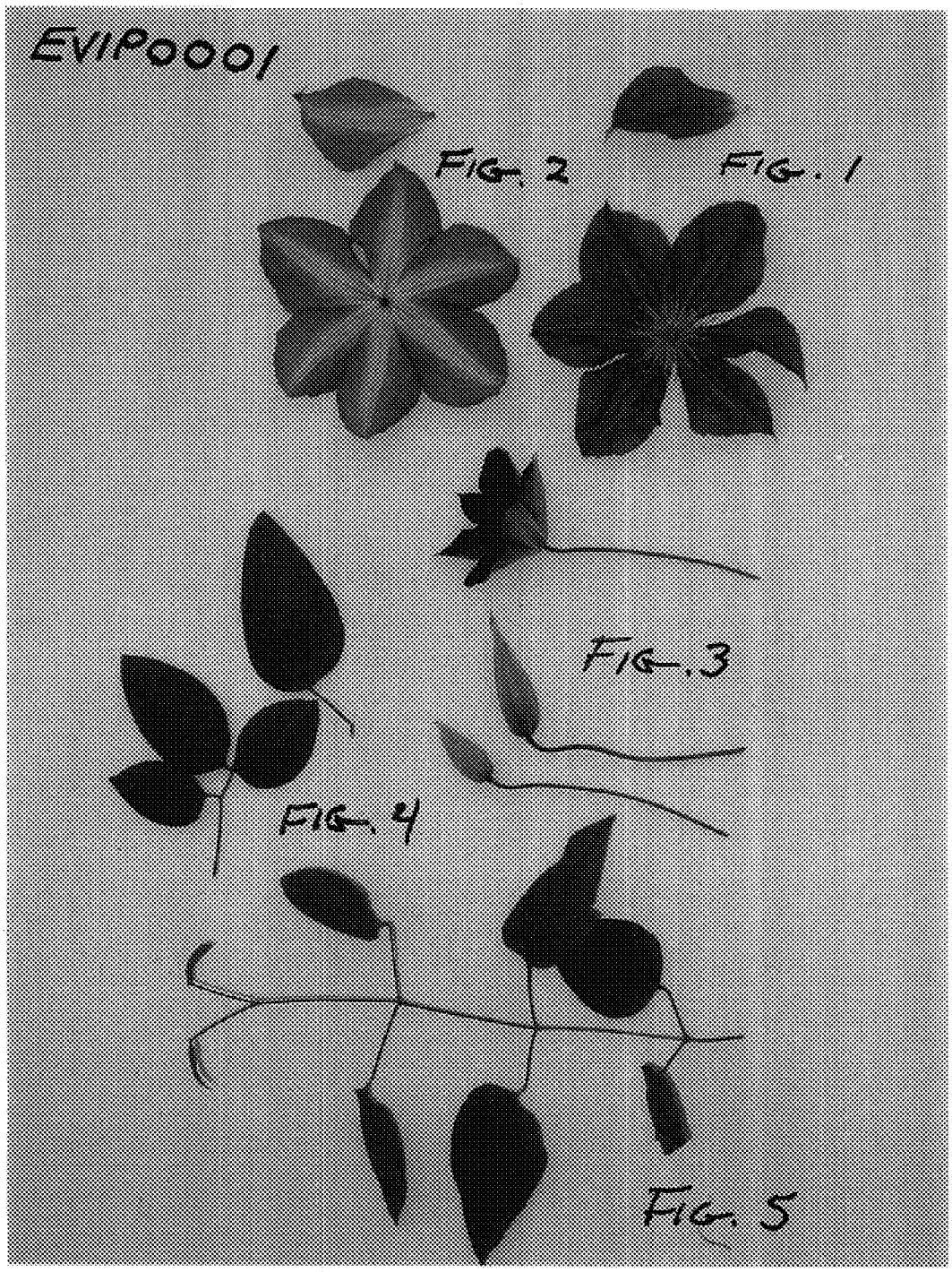
FIG. 1 Bloom, upper side.
FIG. 2 Bloom, lower side.
FIG. 3 Partially opened flower, flower bud closed, and flower bud at ¼ opening.
FIG. 4 Mature leaves.
FIG. 5 Stem and juvenile foliage, showing attachment of leaves.

'EVIpo001' in its entirety growing on a support structure.

DETAILED DESCRIPTION OF THE VARIETY

The following is a detailed description of 'EVIpo001', as observed in its growth throughout the flowering period in glasshouses at Domarie Vineries Les Sauvagees, St. Sampsons, Guernsey, Channel Islands, United Kingdom. Observed plants were cultivated for a period of 24 months in 2 liter containers. Certain phenotypical characteristics of the variety may vary under different environmental, cultural, agronomic, seasonal, and climatic conditions. Color references are made using The Royal Horticultural Society (London, England) Colour Chart, 1995.

For a comparison, the nearest existing *Clematis* variety is 'Rhapsody', a non-patented variety. Chart 1 details several physical characteristics of 'Evipo001' and the comparison variety.

CHART 1

| | 'EVIpo001' | 'Rhapsody' |
|---|---|---|
| Flower diameter | 90 mm to 120 mm. | 100 mm to 150 mm. |
| Typical growth in one season | 2.5 m to 3.0 m. | 2.0 m to 2.5 m. |
| Peduncle aspect | Horizontal to slightly nodding. | Erect to horizontal. |
| Tepal count | Normally 4 to 6. | Normally 6 to 8. |

FLOWER AND FLOWER BUD

Blooming habit: Summer. Generally flowers in June, July, August, and September.

Flower bud:

*Size.*—30 to 40 mm in length. Bud diameter is 12 to 15 mm.

*Bud form.*—Long ovoid.

*Bud color.*—Green Group 138C at ¼ opening.

Peduncle:

*Surface.*—Smooth.

*Length.*—90 to 120 mm average length.

*Color.*—Yellow-Green Group 144B maturing to Red-Purple Group 61A.

*Strength.*—Between horizontal and slightly nodding.

Receptacle: None.

*Borne.*—Borne on compound cymes.

Flower bloom:

*Size.*—90 to 120 mm in diameter.

*Form.*—Opens flat with tepals recurving.

*Depth.*—Little depth (5 to 10 mm) but anthers and stigma protrude giving the flower a total depth of 15 to 20 mm.

*Fragrance.*—None to very light.

*Lasting quality on plant.*—7 to 12 days.

*Lasting quality as a cut flower.*—2 to 5 days.

Tepals:

*Tepal color.*—Upon opening, upper and lower surfaces are Violet Group 88D. After opening, upper and lower surfaces are Violet Group 88D.

*Variations.*—The longitudinal region of the tepal undersurface may show a slight white central bar, White Group 155A, along its length. As the flower ages general tonality fades slightly to Violet Group 88C.

*Quantity.*—Single. Average range is 4 to 6 tepals.

*Shape.*—Individual tepal shape is elliptical to ovate. Tepal base shape is acute.

*Cross section.*—Normally straight.

*Undulation of margin.*—Entire.

*Tepal apex.*—Acute.

*Recurvature of tip.*—Tip recurves.

*Persistence.*—Drop off cleanly.

*Arrangement.*—Tepals are arranged regularly.

Reproductive organs:

*Pollen.*—Quantity: Below average. Color: Yellow Group 11B.

*Anthers.*—Size: Small, 3 to 5 mm. Color: Yellow-Green Group 145C. Arrangement: Regular.

*Filaments.*—Color: White Group 155A.

*Pistil count.*—20 to 30.

*Stigmas.*—Protrude from anthers as flower ages.

*Styles.*—Yellow-Green Group 145C.

PLANT

Plant form: Climbing and spreading depending on host.

Plant growth: Vigorous.

Height: Seasons growth attains 2.5 to 3.0 meters.

Spread: Typically 1 to 2 meters.

Hardiness: Trials to date show the variety hardy in USDA Zones 4–9.

Stems:

*Color.*—Young wood: Red-Purple Group 61A. Older wood: Light Brown (actual RHS designation Greyed-Orange 165C).

*Internodes.*—Shape: Cylindrical. Length: 100 to 150 mm.

*Petioles.*—Size: 60 to 80 mm. Color: Green Group 143A maturing to Red-Purple Group 61A.

*Bark.*—Young wood: Smooth. Older wood: Smooth.

Plant foliage: Deciduous. Trifolate with three broad elliptical to ovate leaflets. Can occasionally be simple.

*Terminal leaflet size.*—60 to 80 mm (l)×40 to 50 mm (w).

*Abundance.*—Above average.

*Color.*—Top: Green Group 137B. Bottom: Green Group 137B.

Plant leaves and leaflets:

*Stipules.*—Absent.

*Petioles.*—Size: 60 to 80 mm in length. Color: Green Group 143A maturing to Red-Purple Group 61A.

*Petioloule.*—Length: 10 to 40 mm. Color: Green Group 143A maturing to Red-Purple Group 61A.

*Leaf edge.*—Terminal leaflet margin is entire.

*Leaflet shape.*—Base: Rounded. Apex: Acute.

*Texture.*—Smooth.

*Surface.*—Upper side: Rough with a matte finish. Lower side: Rough with a matte finish.

*Thickness.*—Thick.

*Glossiness.*—Matte Finish.

Disease resistance: Subject to any disease that normally attacks the species, however the variety is more tolerant to Botrytis and Wilt than some *Clematis*.

It is claimed:

1. We claim a new and distinct variety of *clematis* plant, substantially as herein shown and described, due to its abundant violet blue flowers with good keepability, attractive long lasting foliage and compact growth, year round flowering under glasshouse conditions, suitability for production from softwood cuttings in pots, durable flowers and foliage which make the variety suitable for distribution in the floral industry.

* * * * *

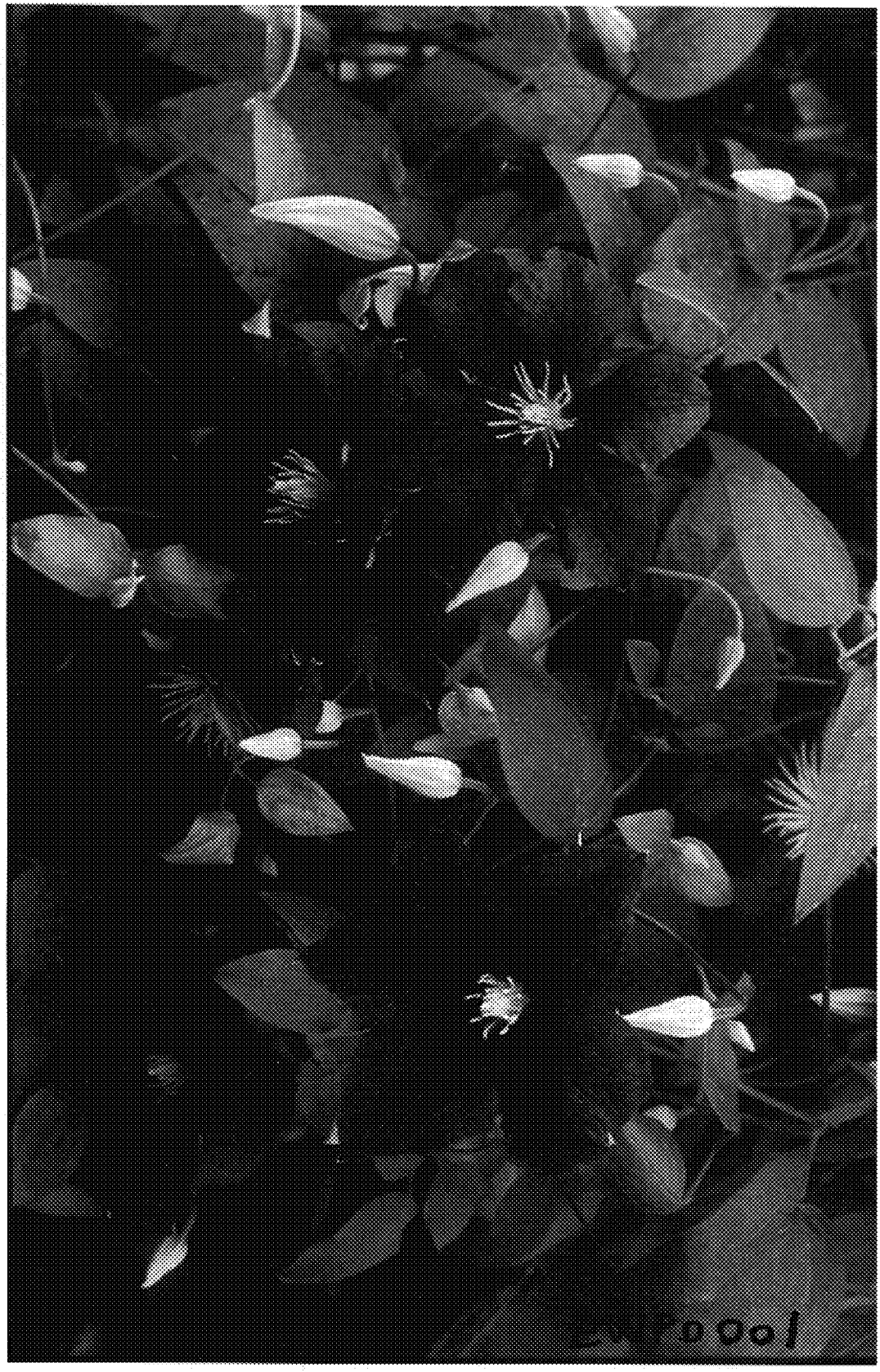

EVIP0001